United States Patent [19]
Zanelli et al.

[11] Patent Number: 6,024,703
[45] Date of Patent: Feb. 15, 2000

[54] ULTRASOUND DEVICE FOR AXIAL RANGING

[75] Inventors: Claudio I. Zanelli, Sannyvale; Jeffrey J. Giba, Marina Valley; Michael A. Davis, San Carlos; Douglas Murphy-Chutorian, Sunnyvale, all of Calif.

[73] Assignee: Eclipse Surgical Technologies, Inc., Sunnyvale, Calif.

[21] Appl. No.: 08/852,977

[22] Filed: May 7, 1997

[51] Int. Cl.⁷ ...................................................... A61B 8/00
[52] U.S. Cl. ............................................ 600/437; 600/459
[58] Field of Search .................................. 600/466, 467, 600/443, 468

[56] References Cited

U.S. PATENT DOCUMENTS

| | | |
|---|---|---|
| 4,936,281 | 6/1990 | Stasz . |
| 5,109,830 | 5/1992 | Cho ............................................. 128/4 |
| 5,196,006 | 3/1993 | Klopotek . |
| 5,409,000 | 4/1995 | Imran . |
| 5,544,656 | 8/1996 | Pitsillides et al. . |
| 5,662,124 | 9/1997 | Wilk . |
| 5,724,975 | 3/1998 | Negus et al. . |
| 5,893,848 | 3/1999 | Negus et al. ............................... 606/41 |

FOREIGN PATENT DOCUMENTS

| | | |
|---|---|---|
| 196 06 610 A1 | 8/1979 | Germany . |
| 195 37 084 A1 | 4/1997 | Germany . |
| WO 97/25101 | 7/1997 | WIPO . |
| WO 98/17185 | 4/1998 | WIPO . |
| WO 98/30144 | 7/1998 | WIPO . |
| WO 98/38916 | 9/1998 | WIPO . |

*Primary Examiner*—Scott M. Getzow
*Assistant Examiner*—Maulin Patel
*Attorney, Agent, or Firm*—Ray K. Shahani; Janet Kaiser Castaneda

[57] ABSTRACT

A treatment tool such as a catheter, MIS or other surgical tool apparatus for placement within a heart chamber, organ aperture or other body opening and axial ranging therein, the apparatus particularly adapted for laser-assisted percutaneous transmyocardial revascularization (MTR). At the distal end of the tool is an annular ultrasound transducer with associated structure, positioned to transmit ultrasound signals substantially axially aligned with the axis of the treatment tool to the cardiovascular tissue, the transducer further receiving returning signals from the cardiovascular tissue to be treated. In a preferred embodiment, the transducer comprises a piezoelectric crystal material. The transducer assembly is attached to the distal tip of the tool such that a laser delivery means or other functional device can be extended through the lumen of the tool and the annular ultrasound transducer. In a preferred embodiment, the invention is a modular ultrasound device capable of being detachably attached to a steerable catheter, MIS or other surgical tool apparatus. The system also comprises a signal interface extending from the ultrasound transducer and signal processing component operatively connected to the signal interface for real time determination of at least one boundary surface of cardiovascular tissue relative to one or more positions of the distal tip of the treatment tool. A method of delivering laser energy to tissue is disclosed, the method including the steps of positioning the firing tip of a laser delivery means adjacent the front surface of the tissue, delivering laser energy to the tissue, transmitting ultrasound energy to the tissue, receiving ultrasound signals reflected from at least the rear surface of the tissue, and determining the distance betwveen the firing tip of the laser delivery means and the rear surface of the tissue. In a preferred embodiment, the method includes quantitative determination of the contractility or motion of the beating heart, such that changes in the depth of tissue can be used to control the channel depth or other treatment parameters. Retrolasing can also be achieved by mechanically piercing the tissue to a determined depth based on axial ranging measurements, and retracting the treatment tool while simultaneously delivering laser energy therefrom.

31 Claims, 7 Drawing Sheets

ULTRASOUND DEVICE FOR AXIAL RANGING

FIELD OF THE INVENTION

The present invention relates generally to catheters, MIS and other surgical tools for therapeutic applications. More particularly, the invention relates to a catheter, MIS or other surgical tool fitted with an ultrasound transducer that makes it particularly suited for determining the depth of dynamic tissue in beating heart laser-assisted transmyocardial revascularization (TMR), but not limited to such application. As the ultrasound transducer is fired, an acoustic wave is generated and a signal is reflected back to the transducer from anatomical structures, thus providing information on the position of the catheter, MIS or other surgical tool in relation to the anatomical structure.

BACKGROUND OF THE INVENTION
Transmyocardial Revascularization

In the treatment of heart disease, one method of improving myocardial blood supply is called *transmyocardial revascularization* (TMR), the creation of channels in the myocadium of the hear. The procedure using needles in a form of surgical "myocardial acupuncture" has been used clinically since the 1960s. Deckelbaum. L. I., Cardiovascular Applications of Laser Technology, *Lasers in Surgery and Medicine* 15:315–341 (1994). The technique relieves ischermia by allowing blood to pass from the ventricle through the channels either directly into other vessels communicating with the channels or into myocardial sinusoids which connect to the myocardial microcirculation.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures recurred with the advent of medical lasers used to create TMR channels. Histological evidence of patent, endothelium-lined tracts within laser-created channels shows that the lumen of laser channels can become hemocompatible and resists occlusion. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the epicardial surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the epicardial surface of the heart to create the desired number of channels.

Since TMR involves creating channels through the endocardium into the lower left chamber of the heart, it is also desirable to create TMR channels percutaneously, i.e., by extending a catheter apparatus through the vasculature into the ventricle and creating the channels through endocardial surfices and into myocardium. Performing such percutaneous TMR is desirable for a number of reasons. Percutaneous catheter procedures are typically less traumatic to the patient compared to surgical procedures. Adhesions between the pericardial sac and epicardium are eliminated. Percutaneous TMR with a catheter apparatus also offers an alternative solution to persons who are not candidates for surgical procedures.

TMR procedures generally involve creating a plurality of channels within the myocardium. In performing the procedure, particularly percutaneously, it is desirable to have information relating to the depth of channels created, placement of the channels relative to the heart walls and wall thickness of the beating heart. None of the TMR or atherosclerosis devices described above or elsewhere provide such information.

Ultrasound

Ultrasound systems are widely used in medical applications. Sound waves above the frequency normally detectable by the human ear, that is, about 16 to 20 kHz are referred to as ultrasonic waves.

U.S. Pat. No. 4,576,177 issued Mar. 18, 1986 to Webster, Jr. teaches a catheter for removing arteriosclerotic plaque. The apparatus comprises a catheter having an optical fiber for transmitting laser energy and an ultrasound transducer. One embodiment of the device is operated in two different modes—a pulse-echo mode and a pulsed-Doppler mode. In the pulse-echo mode an electrical impulse delivered to the transducer transmits an ultrasound pulse, returning echoes thereof causing electrical "signature" signals. In the pulsed-Doppler mode, ultrasonic echoes from tone bursts generated in response to electrical bursts transmitted to the ultrasound transducer are used to determine the blood flow velocity at two selected distances from the catheter tip. The tissue signature and the change in blood flow velocity are used to determine the presence of occlusions in blood vessels.

U.S. Pat. No. 4,658,827 issued Apr. 21, 1987 to He et al teaches an ultrasound scanner for tissue characterization. A method and system are disclosed for simultaneously obtaining accurate estimates of the attenuation coefficient of the tissue and an index describing the heterogeneity of the scatterers within the tissue. According to the invention, there is provided a method and apparatus for tissue characterization by transmitting ultrasound energy into the sample tissue, and receiving and processing return echo signals.

U.S. Pat. No. 4,672,963 issued Jun. 16, 1987 to Barken teaches an apparatus and method for computer controlled laser surgery using an ultrasound imaging system. The position of the laser energy delivery device is monitored with an ultrasound probe. The probe, in conjunction with a computer system, provides a multiplicity of cross-section images of the portion of body tissue within the range of emitted destructive radiation.

U.S. Pat. No. 5,109,859 issued May 5, 1992 to Jenkins teaches an ultrasound guided laser angioplasty system. This system is also directed to the application of removal of atherosclerotic plaque from coronary arteries of patients with heart disease. A probe with a phased-array ultrasound transducer will produce images of vascular tissue acquired in a plane that is 30° forward of the tip of the catheter to prevent vascular perforation. As above, the catheter provides primarily lateral imaging.

U.S. Pat. No. 5,158,085 issued Oct. 27, 1992 to Belikan et al. teaches a lithotripsy ultrasound locating device using both a locating and a therapy transducer in a fixed relationship. One or more locating ultrasound transducers, each axially rotatable and extendable, generate a signal representing the distance between the locating transducer and the focus of the second transducer, used to transmit therapeutic amounts of ultrasound for fragmentation of a concretion. The locating transducers have two or more crystal rings, thus having two or more focal ranges, and operate according to annular phased-array principles.

U.S. Pat. No. 5,313,950 issued May 24, 1994 to Ishikawa et al. teaches another ultrasound probe. A rotor moves and/or rotates a piezoelectric transducer and/or a reflector and is driven by a stator outside the object under examination. Both forward as well as lateral firing of ultrasound is taught for obtaining sectional views. However, such rotating mirror technology is distinctly different from the ranging application disclosed herein.

U.S. Pat. No. 5,350,377 issued Sep. 27, 1994 to Winston et al. teaches a medical catheter using optical fibers that transmit both laser energy and ultrasound imaging signals. An external transducer couples to the optical fibers and pulse echoes are received and transmitted back to the transducer along the same optical fibers. Visualization is limited to images as to the configuration, location and character of the tissue in the area of atherosclerotic plaques.

As is evident by a review of the ultrasound imaging prior art, including the foregoing, catheters and other tools for TMR having axial ranging capability, in the sense of determination of the distance from the tip of the firing laser delivery means at a first wall of the heart to a second wall of the heart are virtually unknown. Determination of tissue depth viewed in a forward direction, such as in myocardial tissue for forming TMR channels, would be highly advantageous so as to prevent unwanted perforation of a heart wall and/or to form channels of selected depths.

ADVANTAGES AND SUMMARY OF THE INVENTION

Thus, it is an advantage of the present invention to provide a catheter, MIS or other surgical tool apparatus and method of use for percutaneous and other surgical procedures, including percutaneous, MIS and surgical TMR, or any stimulation procedure, which overcomes the limitations of the prior art.

It is another advantage of the present invention to provide such an apparatus with an ultrasound guidance system to provide visualization, depth determination, in particular tool tip-to-tissue wall distance in tissue for controlled treatment as desired, in particular to prevent perforation of epicardial tissue in percutaneous TMR.

An additional advantage of the present invention allows determination/visualization of the spatial dynamics of the tissue of a beating heart, i.e., one in which the wall depth is constantly changing.

It is a further advantage of the present invention to provide such an apparatus wherein the ultrasound guidance system is small, compact and durable, and either integral with the tip of the tool or modular, interchangeable and replaceable.

Yet a futher advantage of the present invention is to provide such an apparatus for percutaneous, MIS or other surgical placement within a heart chamber, organ aperture or other body opening, the apparatus having at least one central lumen extending along at least part of the length of the tool for guiding a laser delivery means or other functional device to selected surfaces of the heart chamber, organ aperture or other body opening for laser or other treatment thereon, particularly adapted for laser-assisted transmyocardial revascularization (TMR).

One more advantage of the present invention is to provide such ultrasound apparatus with ranging visualization means enabling visualization of piercing of a heart wall, advancement of the piercing tip to a selected depth within myocardium, confirmation of such depth, and controlled, visualized withdrawal of the firing tip during laser activation for TMR.

In summary, the present invention is a catheter, MIS or other surgical tool apparatus for placement within a heart chamber, organ aperture or other body opening. The apparatus has at least one lumen extending at least partially through the tool for guiding a laser delivery means or other functional device to selected surfaces of a heart chamber, organ aperture or other body cavity for laser or other treatment thereon, and is particularly adapted for laser-assisted percutaneous transmyocardial revascularization (TMR).

At the distal end of the tool are an ultrasound transducer and associated structure. In a preferred embodiment, the transducer comprises piezoelectric crystal material. The transducer assembly is attached to the distal tip of the tool such that a laser delivery means or other functional device can be extended through the lumen of the tool adjacent the distally mounted ultrasound transducer.

In a preferred embodiment, the invention is a modular catheter, MIS or other surgical tool ultrasound guidance system capable of being assembled and operated, as desired, in combination with, but not limited to, a steerable catheter, MIS or other surgical tool apparatus with a deflectable end portion, a modular fiber advance handpiece unit, and other functional devices including fiber advance depth control mechanism, visualization means, drug delivery apparatus, etc.

For percutaneous TMR, the catheter is modular and is designed to be placed into the vasculature of the patient and steered therethrough until the distal tip is adjacent a selected portion of tissue, such as on an endocardial surface within the left ventricle.

Electrical excitation of the piezoelectric crystal will cause ultrasound waves to propagate therefrom in a forward direction. Returning echoes produced by either anatomical or catheter structures are detected by the transducer and converted to electrical signals. These signals can be correlated with the distance from the transducer to a laser delivery means, to a surface to be penetrated by a laser delivery means, and to an opposing surface generally perpendicular to the site of initiation of the TMR channel. Additionally, the changes in myocardial wall thickness of the beating heart can be detected based on detection of signals propagating from the epicardial and/or endocardial surface of the heart while expanded and while contracted. Thus, the distal tip of a laser delivery means, such as an optical fiber or fiber bundle or other finctional device, can be extended into moving myocardium from an endocardial surface a selected, controlled distance and undesired perforation of the epicardium can be avoided.

The methods and apparatus of the present invention are suitable and intended for use not only percutaneously with any catheter tools but for use with any other MIS and other surgical tools, laser handpieces, other laser delivery systems, etc.

Numerous other advantages and features of the present invention will become readily apparent from the following detailed description of the invention and the embodiments thereof from the claims and from the accompanying drawings.

DETAILED DESCRIPTION OF THE PREFERRED EMBODIMENT

Preferred Apparatus

Figure 1:
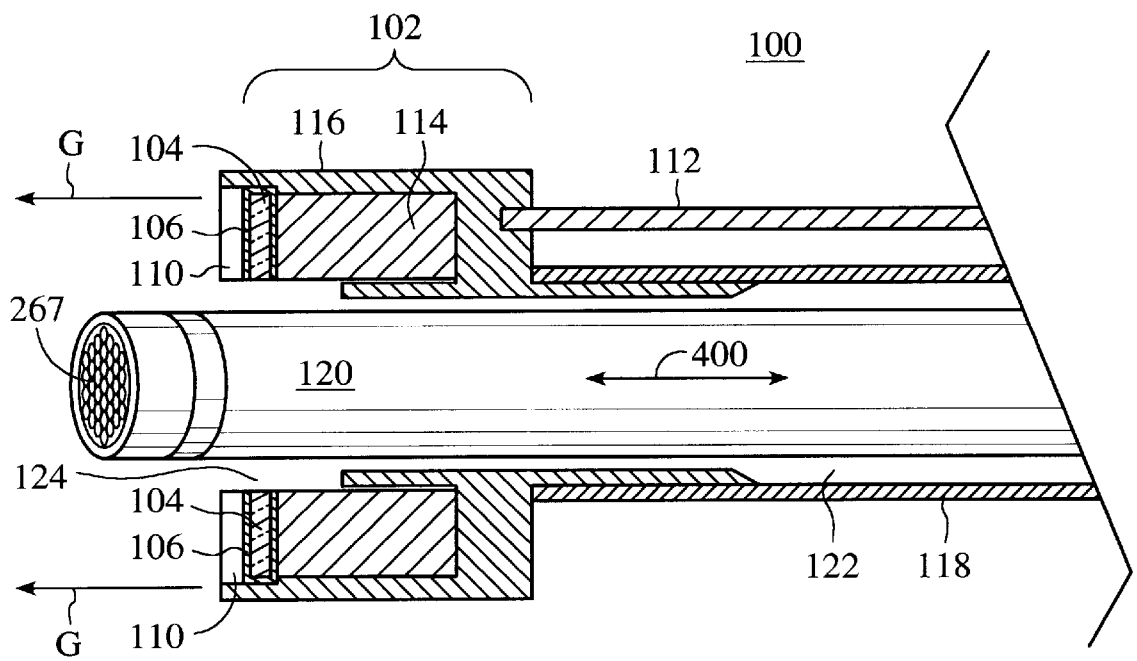
FIG. 1 is a representative section view of a preferred embodiment of an ultrasound guidance system 100 of the present invention.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function will have like reference numerals associated therewith.

FIG. 1 is a representative section view of a preferred embodiment of an ultrasound guidance system 100 of the present invention. It will be understood that the drawing is representative and exemplary only, and such ultrasound ranging apparatus can be part of any treatment tool, interventional device, catheter, any MIS or other surgical tool, laser handpiece, or other laser delivery system.

At the distal end of the treatment tool the distal tip 102 comprises an ultrasound transducer and associated structure. In the embodiment shown, the transducer comprises a generally flat annulus shaped piezoelectric crystal 104. A thin gold trace 106 or other layer of electrically conductive material covers the crystal 104. An outer acrylic matching layer 110 over the gold trace 106 protects and insulates the gold trace 106 and is designed to optimize acoustic efficiency. The gold trace forms an electrically conductive layer around the crystal 104 and is electrically connected to a coaxial cable 112 which extends through conductive rubber backing material 114.

A polymeric housing 116 in the shape of a cup holds the rubber backing material 114, piezoelectric crystal or other ultrasound transducer 104 with gold trace 106 and acrylic matching layer 110, with the coaxial cable 112 extending therefrom. It will be understood that the coaxial cable 112 is but one possible signal interface which couples signals sent to and received from the ultrasound transducer 104 with a signal processing component. The entire assembly is coupled to the distal tip 102 of the tool 100, such that a laser delivery means 120 or other functional device can be extended through a central lumen 122 of tool 100 and through a generally circular opening 124 in the annulus shaped ultrasound crystal 104.

It will be understood that the material of construction as well as the shape of the ultrasound crystal can be changed and that the generally flat annulus shaped piezoelectric crystal 104 is but one of the preferred embodiments. Numerous types of ultrasound transducer materials are known, and the class of materials known as piezoelectrics are but one. Likewise, different shaped crystals are known and readily available, the different shapes having different signal propagating and receiving characteristics. As an example but not to limit the scope of the present invention, the transducer element may have a slightly parabolic shape. Furthermore, a single transducer element can be divided into sections or replaced with a plurality of transducer elements, optionally configured in an array such as a phased array or other. Such configurations comprising more than one transducer element will have associated electrical couplings, drivers, etc.

The term axial ranging refers to the manner in which the ultrasound signals are emitted from the device. The main axis 400 of each of the embodiments is shown. Thus, ultrasound signals are emitted in the general direction G as shown throughout, and signals returning in an opposing direction are detected by the ultrasound assembly.

Figure 2:
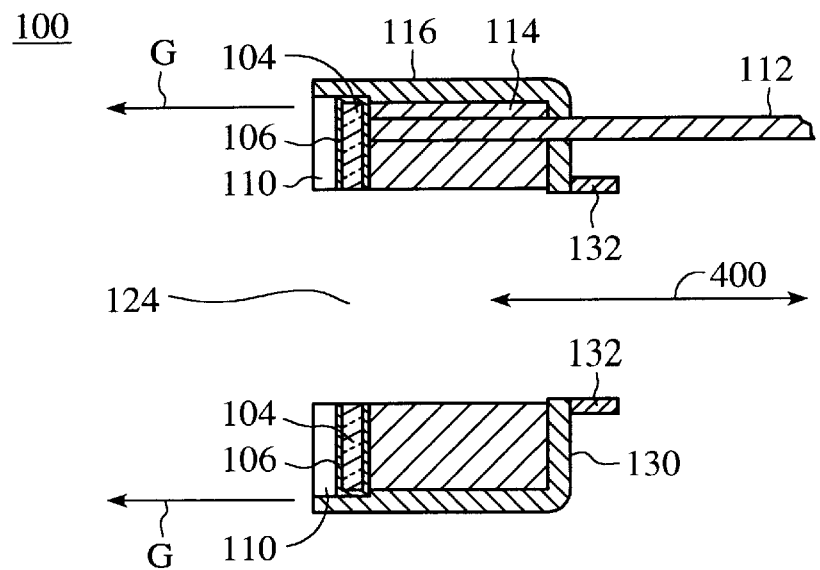
FIG. 2 is a representative section view of a preferred embodiment of a modular ultrasound catheter, MIS or other surgical tool transducer 200 for an ultrasound guidance system of the present invention.

FIG. 2 is a representative section view of a preferred embodiment of a modular catheter, MIS or other surgical tool ultrasound transducer 150 for an ultrasound guidance system of the present invention. As in the prior embodiment, a matching layer 110 covers a gold trace 106. A coaxial cable 112 is used to deliver electrical current to the crystal 104 for excitation as well as to receive current signals produced by acoustic pulses received by the crystal 104. Additionally, a mounting face 130 with a mounting flange 132 provides a means for coupling the modular ultrasound transducer 150, forward looking in the present configuration, to the distal end of a conventional or other type catheter, MIS or other surgical tool. It will be understood by those known in the art that such coupling means includes, and is not limited to, bayonet and other quick connect mounts, screw on or snap on couplings, etc.

Thus, in the preferred embodiment, the invention is a modular ultrasound guidance system capable of being assembled and operated, as desired, in combination with, but not limited to, a conventional catheter apparatus, a steerable catheter apparatus with a deflectable end portion, an MIS or other surgical tool, a modular fiber advance handpiece unit, and other functional devices including fiber advance depth control mechanism, visualization means, drug delivery apparatus, etc.

Figure 3:
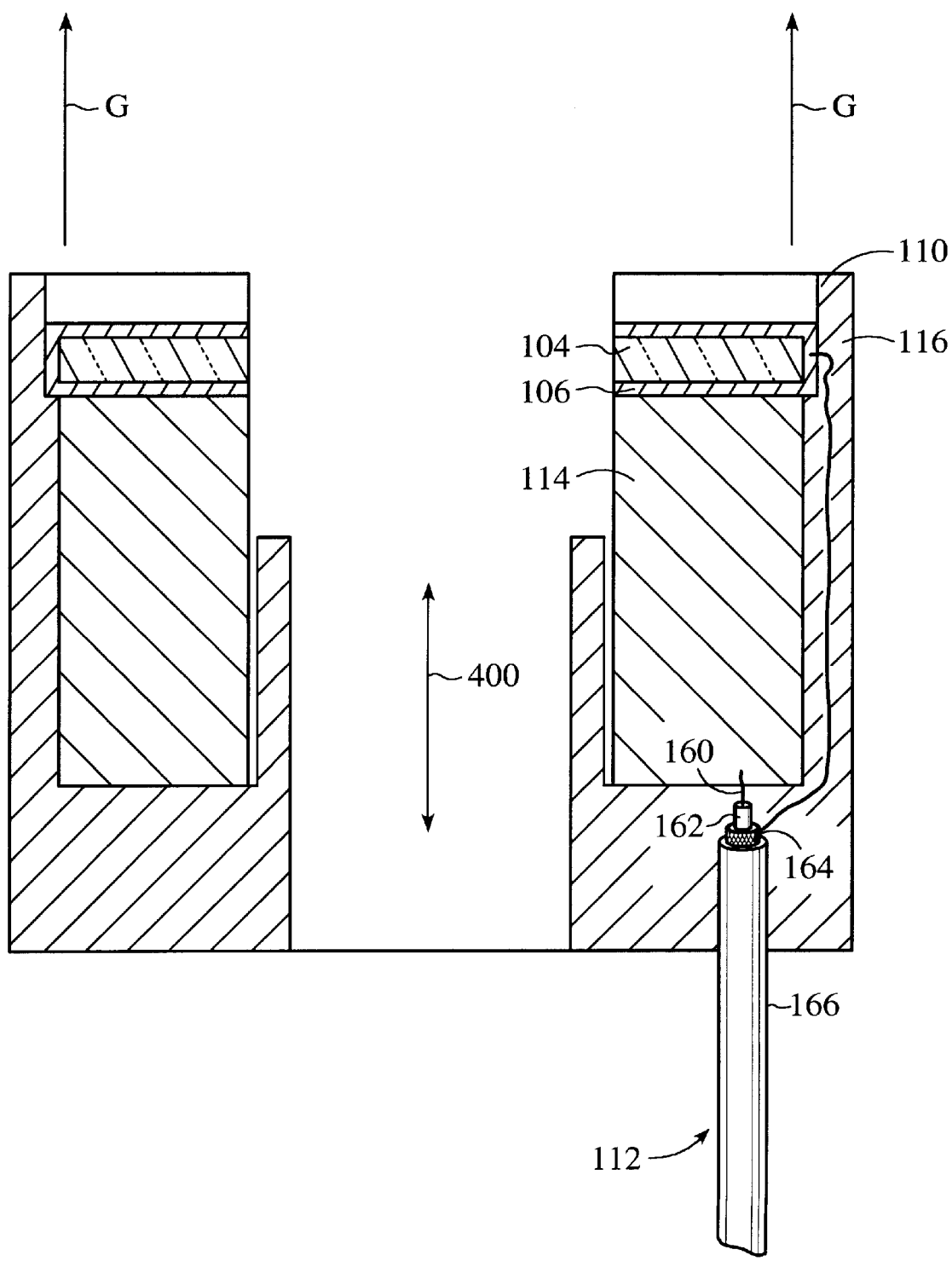
FIG. 3 is a representative detail section view of a piezoelectric crystal 104 of an ultrasound guidance system of the present invention.

FIG. 3 is a representative detail section view of the ultrasound transducer assembly of the present invention. The coaxial cable 112 is comprised of, from the inside out, a conductor wire 160, an insulation layer 162, a shielding layer interface 164 and an outer jacket 166. The stripped central conductor 160 is inserted through housing 116 into backing material 114 below the crystal 104 and the backing material 114 ma by, and preferably is, conductive. The upper surface 140, lower surface 146 and outer peripheral edge 142 of the transducer crystal 104 are coated with sputtered metal gold trace 106 and the shielding layer interface 164 touches the sputtered metal gold trace 106. It will be understood that the gold layer 106 can be applied in any conventional way, preferably by sputtering, vapor deposition, etc. The shielding layer interface 164 and the central conductor 160 can be electrically connected to the respective gold trace 106 and backing material 114 using simple contact technology, conventional solder, silver or indium epoxy, etc. Thus, applying a voltage across the piezoelectric crystal 104 will excite the crystal and create an acoustic wave. Upon reflection of the wave off an anatomical surface, the acoustic echo will return to the crystal 104 and create a small signal which can be detected and amplified. It will be understood that the transmitter and receiver combination may be a conventional design and/or may be a single, combined module.

Figure 4:
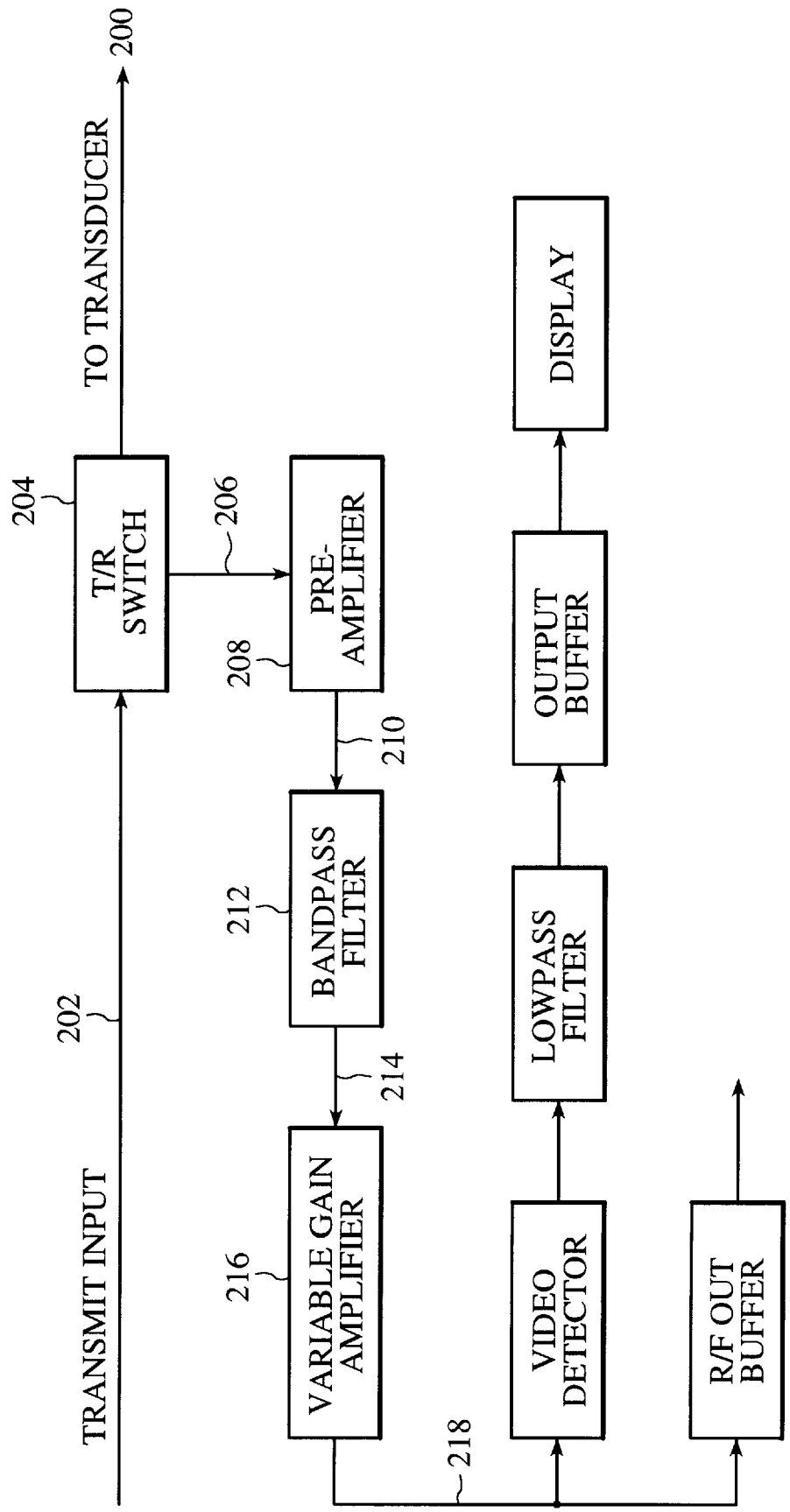
FIG. 4 is a representative electrical schematic RF module block diagram of a preferred embodiment of an ultrasound guidance system of the present invention.

FIG. 4 is a representative electrical schematic RF module block diagram of a preferred embodiment of an ultrasound guidance system of the present invention. Excitation of the ultrasound transducer 200 of the present invention is caused by input signal 202. Input signal 202 is switched to the ultrasound transducer 200 through transmit and receive (T/R) switch 204. The transducer 200 emits a signal in response to every input signal 202. Signals 206 from transducer 200 and echoes are converted to signals which are switched through T/R switch 204 to pre-amplifier 208. Filtering of the amplified signals 210 by bandpass filter 212 and further processing and amplification of the filtered signals 214 by variable gain amplifier 216 produce selected amplified signals 218 representing depth of structure, such as myocardium, which can be further processed as desired.

As shown, such selected amplified signals 218 can be received by RF$_{out}$ buffer 220 for recording the information, etc. A video detector sufficient to cover the range of possible frequencies used in the ultrasound system, such as between about 5 and 20 mHz and more preferably about 15 mHz, provides a signal used to create an A-mode scan for viewing on display 260. It will be understood that the display means 260 can be an oscilloscope, computer monitor, or can be input to a computer and stored. It will further be understood that software processing of emitted pulse data and echo data to calculate signal delay, for determination of depth to a tissue boundary surface, or depth of myocardium from wall to wall, can be achieved using various or custom software.

Figure 5:
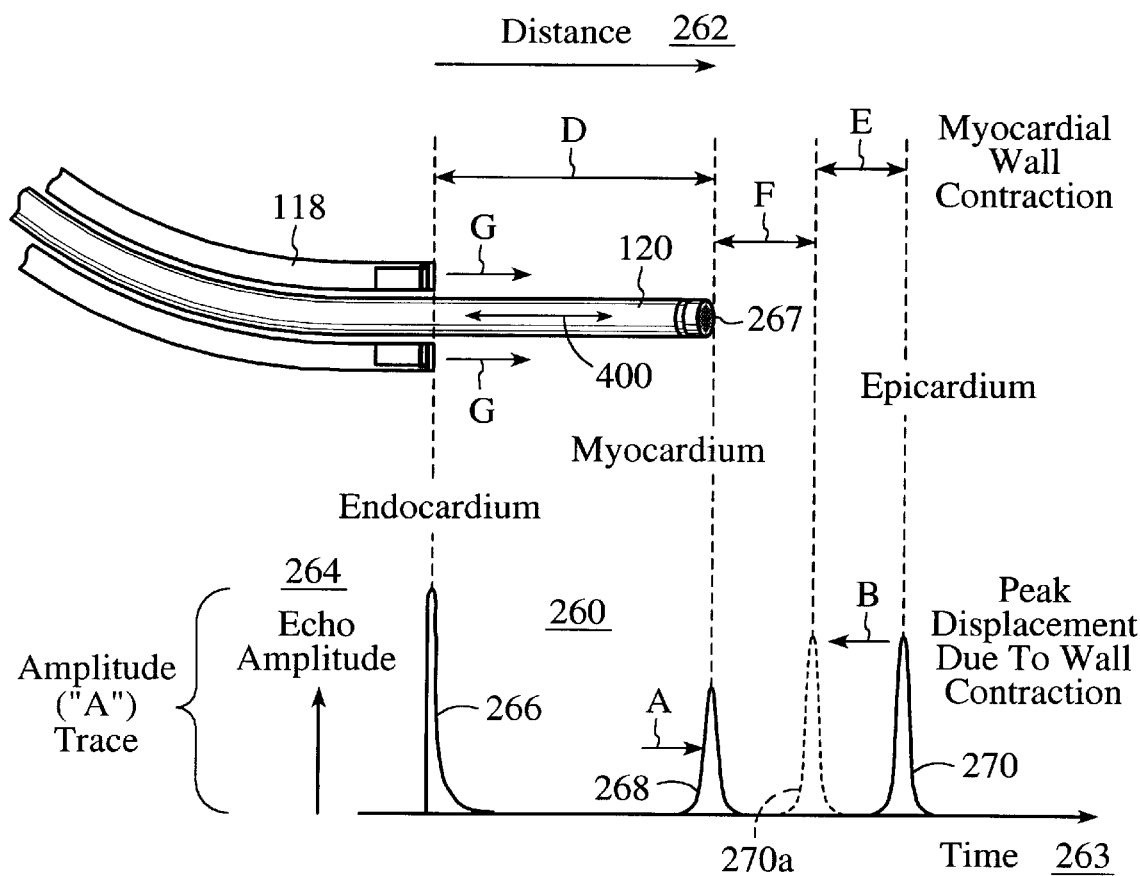
FIG. 5 is a representative A-mode scan display in juxtaposition with a representation with a method of use of a preferred embodiment of an ultrasound guidance system of the present invention.

FIG. 5 is a representative A-mode scan display 260 in juxtaposition with a representation of the method of use of a preferred embodiment of a percutaneous catheter ultrasound guidance system of the present invention for TMR, discussed farther below. It will also be understood that FIG. 5 refers to an ultrasound ranging device comprising a catheter for percutaneous surgery, and the application is TMR from inside the left ventricle into myocardium.

Figure 6A:
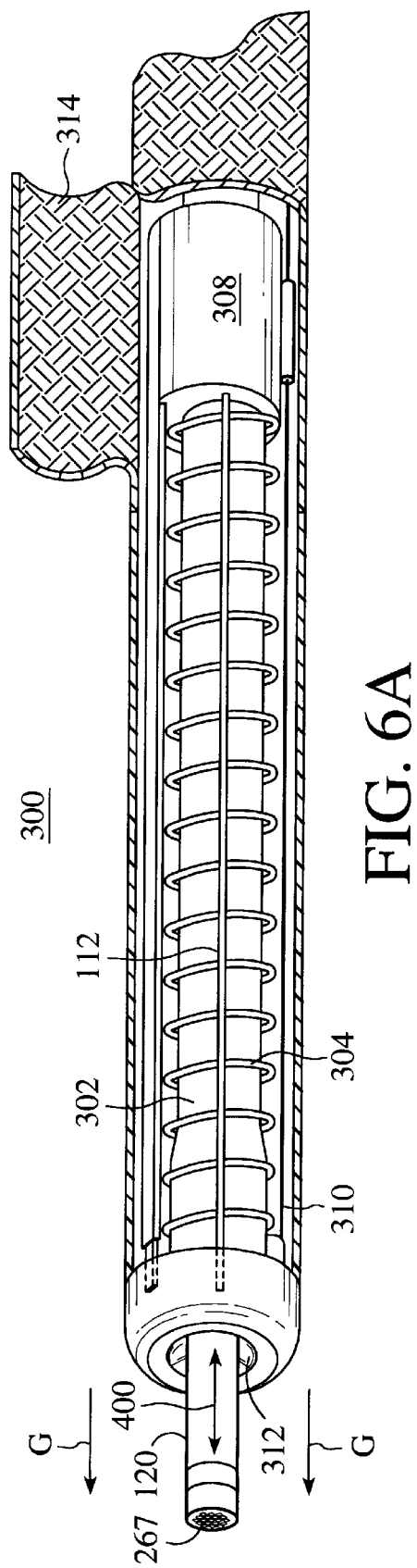
FIGS. 6A and 6B are representative isometric and section views of the distal end and steering means of a preferred embodiment of an ultrasound guidance system of the present invention.
Figure 6B:
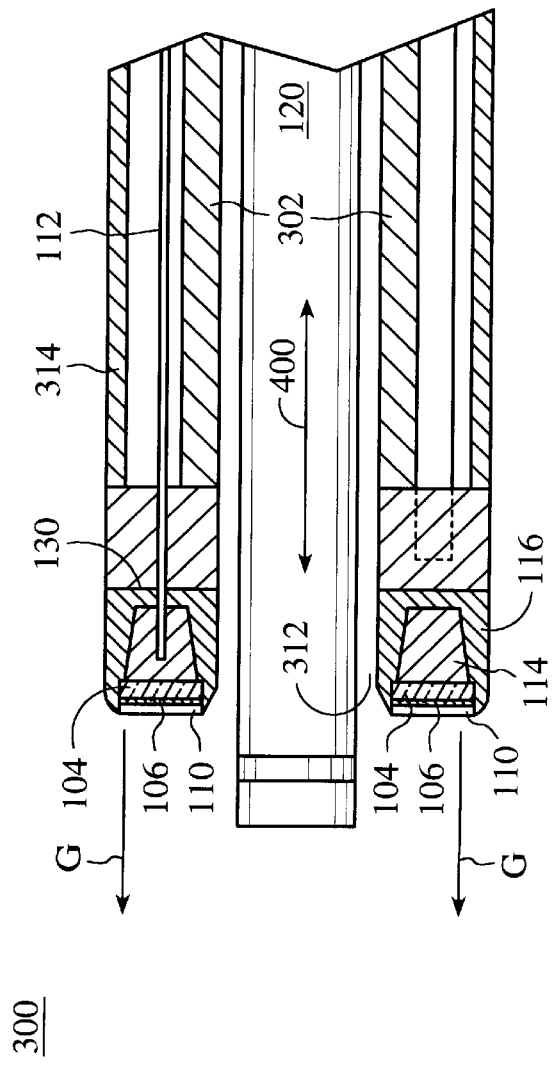

FIGS. 6A and 6B are representative isometric and section views of the distal end and steering means of a preferred embodiment of a TMR catheter ultrasound guidance system 300 of the present invention. As in the prior embodiments, a matching layer 110, gold trace 106, transducer crystal 104, backing 114, coaxial cable 112 and housing 116 are assembled together. Mounting face 130 couples to the distal tip 302 of catheter 300. It will be understood by those known in the art that such coupling means includes, and is not limited to, bayonet and other quick connect mounts, screw on or press fit/snap on couplings, etc.

The catheter 300 is steerable and has steering means as described herein. A central catheter tube 302 terminates in the distal tip 302. A spiral spring member 304 made of a radiopaque material adds visibility to the bend radius of the apparatus and enhances steerability of the apparatus 300. A flat planar, rigid shim 306 couples between the distal tip 302 of the catheter 300 and an intermediate sleeve 308. A pull cable 310 also attaches to the distal tip 302 opposite the annular opening 312 through the distal tip 302 so as to act upon the distal tip 302 and cause deflection of the shim 306 as desired to steer the distal tip 302 to selected regions or surfaces. An outer jacket 314 protects the catheter assembly 300. Embodiments of the steerable catheter apparatus of the present invention without the ultrasound guidance system are described in U.S. patent application Ser. No. 08/5,876, 373, filed Apr. 3, 1997 and entitled STEERABLE CATHETER, and incorporated herein in its entirety.

With regard to the coaxial cable 112, by utilizing cabling of about 0.0075" diameter, as currently available and manufactured by companies such as Temp-Flex Cable, Inc., located in Graften, Massachusetts, a reduction in the size limitations and an increase in the working channel spaces of the catheter apparatus shown or other catheter and/or surgical devices is possible.

Additionally, the ultrasound device may be used with curved or pre-bent catheters for delivery of a single optical fiber with or without a lens device for operatively, selectively and/or controllably directing laser energy.

Preferred Methodology

It is well understood that the time for return of an echo from a distance d is given by the following equation:

$$t = 2\frac{d}{V_s}$$

where $V_P$ is the velocity of longitudinal sound waves, i.e., approximately 1540 m/s in myocardial tissue. Therefore, algorithms for generating the A trace consist of detecting the envelope of the received RF signal. These algorithms are known in the areas of echo ranging with ultrasound and radar. In a preferred embodiment, the analytic magnitude is used, which consists of computing the Fourier transform, taking the real part of the result, and computing the inverse Fourier transform. If the original echo signal is called $f(t)$, then the amplitude $A(t)$ is computed according to the following equation:

$$A(t) = \int_{-\infty}^{\infty} e^{-izt} R_e \left\{ \int_{-\infty}^{\infty} e^{izt} f(t)\,dt \right\} dz$$

This algorithm is implemented, in the preferred embodiment, in a computer using the fast Fourier transform, well known to those skilled in the art.

Figure 7:
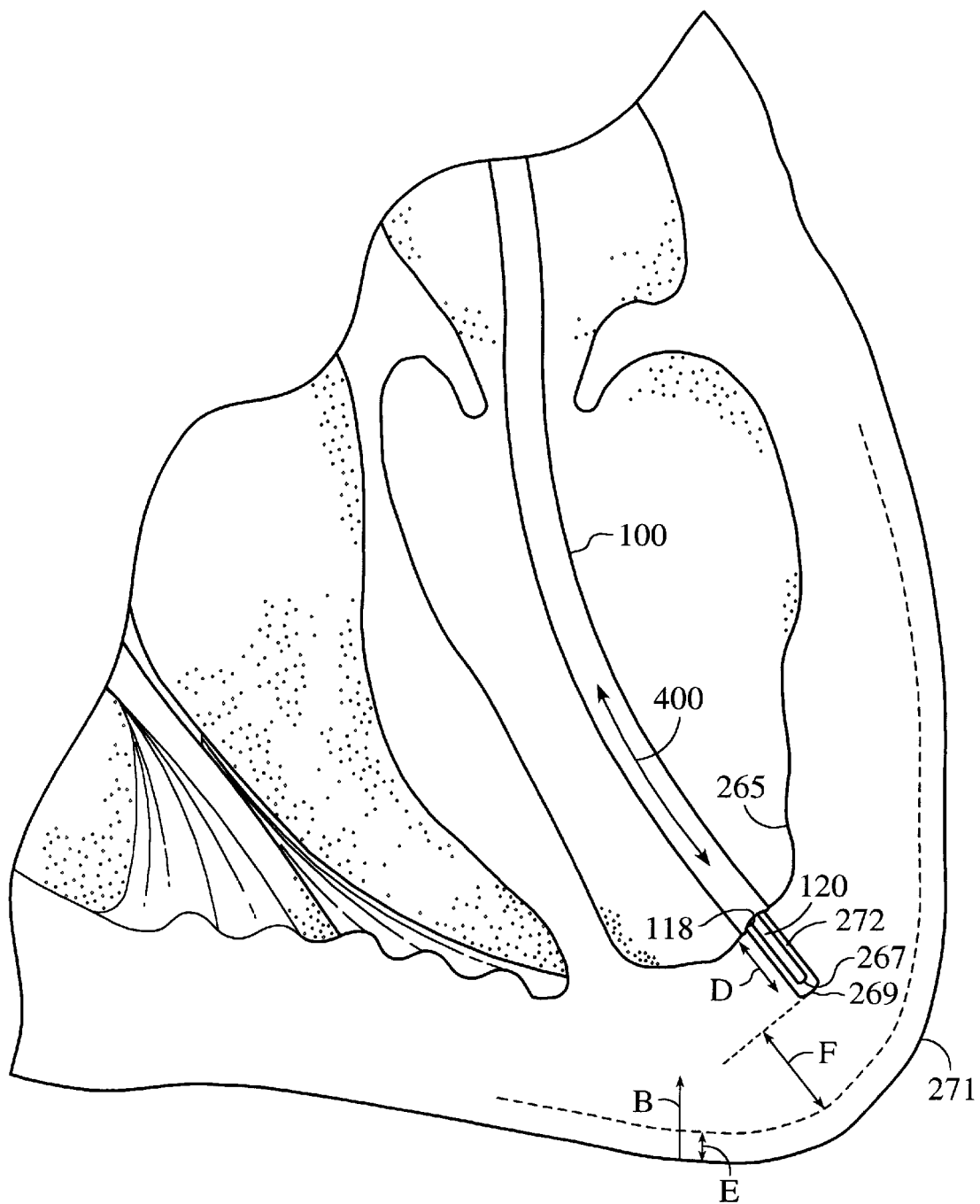
FIG. 7 is a representative drawing of a preferred method of use of a preferred embodiment of the present invention.

Referring again to FIG. 5 as well as to FIG. 7, forward viewing distance 262 is shown on the X-axis and the amplitude of the reflected or echo signal 264 is plotted on the Y-axis. Distance 262 is also correlated with time 263. A first strong amplitude peak 266 is associated with the endocardial surface 265, such surface also referred to herein as a boundary surface of tissue. When the transducer assembly (which will be understood to include, at least, the transducer crystal 104, the gold trace 106, the batching layer 110, the backing material 114, the coaxial cable 112 and the housing 116) of the distal tip 118 of the catheter apparatus 100 of the present invention is firmly in contact with an endocardial surface 265 (not shown in FIG. 5), such surface 265 will be visualized by initial amplitude peak 266. As the laser delivery means 120 is fired, ablation of tissue occurs, and the distal tip 267 of the laser delivery means 120 can be moved forward into the tissue. Continued ablation creates a channel 272 (see FIG. 7) into which the distal tip 267 of the laser delivery means 120 advances for continued channel 272 creation. Thus, a second highly observable amplitude peak 268 on the ultrasound A-mode scan display 260 is formed by the echo returning from the end of the channel 269, and the distal tip 267 of laser delivery means 120, within myocardium. This second peak 268 will be observed to move from left to right, as shown by directional arrow A, as laser ablation and TMR channel 272 formation occurs.

An additional peak 270 is observable at the right side of the display 260. As the ultrasound wave propagates through the tissue, an additional returning echo signal will indicate a structural interface or tissue boundary surface at the position which correlates with the distance to the back wall of the penetrated structure 271, i.e., in this case, the epicardial surface 271 of the heart. However, as is well known, the contractions of the beating heart will tend to cause the wall of the heart to contract in direction B, as well as expand in the opposite direction, thereby causing the wall peak 270 to move in direction C. Thus, an additional wall peak 270a will be observable, which will be a transient peak moving between the positions indicated for peaks 270 and 270a. Thus, as shown, the distance D can be correlated with the length of the channel 272 and the distance E can be correlated with the distance moved by the epicardial surface 271 during contraction of the heart muscle. Therefore, it will be understood that distance F will be correlated with the amount of remaining myocardial tissue between the end of the TMR channel 269 and the epicardial surface 271. This information regarding remaining depth of tissue is vital to the cardiologist in performing TMR. With regard to percutaneous TMR, by controllably forming TMR channels initiating at an endocardial surface, perforation of the epicardium can be avoided.

The ranging device of the present invention will be usefully operated at frequencies between about 500 Hz and about 10 KHz. Such frequencies will be fast enough to allow real-time display of the thickening and thinning of the heart wall brought about as a result of the changes between the systole and diastole components of the beating heart cycle.

Figure 8:
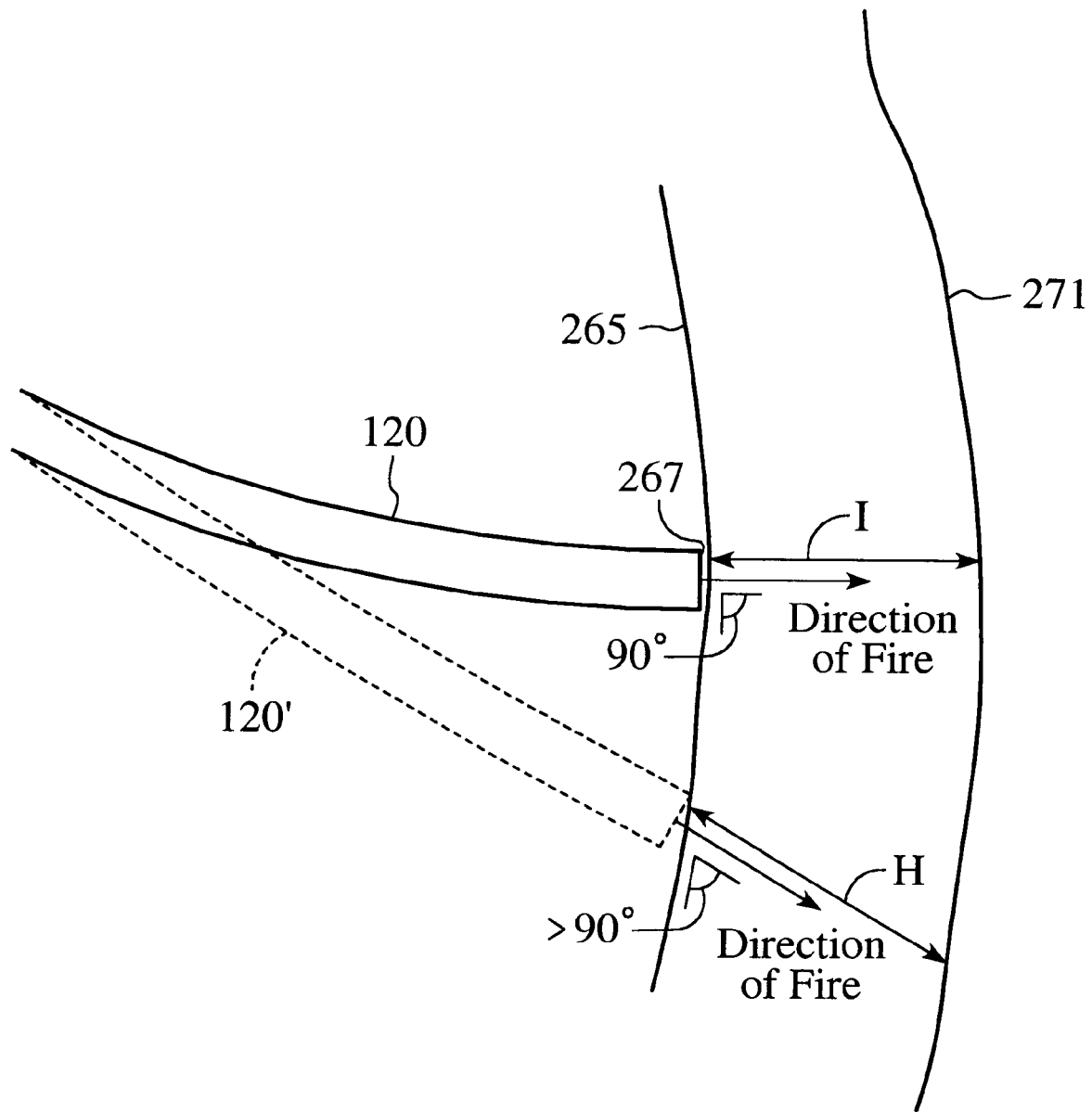
FIG. 8 shows a comparison between the wall thickness or channel depth at 90° or other angulation.

FIG. 8 shows a comparison between the wall thickness or channel depth at 90° or other angulation. Another feature of the present invention, which will require additional calculations to be performed by the signal processing means software or logic, is the ability to confirm perpendicular or other angle wall penetration by the laser delivery means or other interventional device. It will be understood, that if the distance H is greater than the distance I, the distance I being the perpendicular distance from the tip 267 of the laser delivery means 120 to some other anatomical structure interface and the distance H being the distance in a non-perpendicular direction of laser delivery means 120', to the same anatomical structure interface. In other words, when the distance H is greater than the distance I, the angle of penetration of the laser delivery means 120 or other interventional device will be other than 90°.

Referring to FIG. 7, another modality of operation of the present invention is referred to as "retrolasing". In retrolasing, the catheter, MIS or other surgical device preferably has a piercing tip. In the context of percutaneous TMR in the left ventricle, retrolasing is accomplished by inserting the distal tip 267 of the laser delivery means 120 through a mechanically formed perforation in the epicardium 265. The distal tip 267 is advanced a selected distance D into myocardium and the location of the distal tip 267 is confirmed using the ultrasound ranging apparatus of the present invention, such as by visualization on an oscilloscope, computer monitor or other display means, as shown in FIG. 5. Once the tip 267 is placed where desired and the placement confirmed on the ranging display means, laser delivery can commence, firing the laser will initiate creation of a TMR channel 272 and the firing tip 267 is retracted simultaneously with viewing and continued delivery of laser energy. Additionally, the laser can be configured to automatically fire only upon confirmation of a threshold depth measurement setting, taking into account the fluctuating wall thickness due to the contractions of the heart. Not only will this enable retrolasing starting at an initial depth of penetration into myocardium, as confirmed by computer software or logic, but it will also confirm normal heart function, i.e., beating of the heart.

As another method for confirming and/or controlling specific heart function, "pacing" of the heart has been described. When pacing the heart with an external pulse generator during a TMR procedure, there is often no positive confirmation that the heart has beat properly or even at all. Therefore, this positive confirmation of heart function, albeit compromised or otherwise imperfect, may be accomplished by using the ultrasound ranging device and methods described herein to detect the heart beat. The ultrasound device could monitor the measured thickness of the myocardium and determine when a change has occurred. The change in thickness of myocardium can be correlated with contraction and/or expansion of the heart. This signal indicating that the heart has beat could be used such that the TMR laser would not fire unless and until this signal is received. Such pacing of the heart is more fully described in co-pending U.S. patent application Ser. No. 08/793,000, filed Feb. 3, 1997 entitled REVASCULARIZATION WITH HEART PACING, as well as U.S. patent application Ser. Nos. 08/852,011 and 08/852013, filed concurrently herewith entitled REVASCULARIZATION WITH LASER BURSTS AND REVASCULARIZATION WITH HEARTBEAT VERIFICATION, both of which are incorporated herein by reference.

Therefore, when a device or method in which a pre-set number of laser pulses, such as a burst of 5 pulses, is used to create the IMR channels, that pre-set number of pulses can be automatically reduced when heart wall thicknesses are reduced to below a predetermined threshold, such as 5 millimeters. This heart wall thickness measurement can be made in essentially real time by the axial ranging devices and methods of the present invention.

By the present disclosure, it will be apparent to those skilled in the art that audible or visual alarms may be incorporated into the apparatus of the present invention. Audible or visual alarms will give the cardiologist advance notice of achievement of threshold TMR channel depth penetration. Such alarms can also be integrated with mechanical as well as electronic interlock systems for the laser, thereby enhancing efficacy and safety of the apparatus and methods described herein. Thus, the apparatus of the present invention may also be configured to include means to automatically stop fiber advance based on the calculated or otherwise determined axial distance of the firing tip of the laser delivery means from the back wall. Such means includes, but is not limited to mechanically or electronically controlled interlock with feedback loop, electrophysiology signal, etc. The present invention will assist the cardiologist in visualizing the tip of the catheter or surgical tool and the distal tip of the laser delivery means, as well as the endocardial wall, in a percutaneous, intra-ventricle procedure, so that identification of contact between the distal tip of the tool or laser delivery means and the heart surface can be made. Such contact identification will allow the operator or cardiologist to avoid applying excessive force upon the head and thus avoid excessive arrhythmagenic forces thereby.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Furthermore, other interventional systems, in addition to lasers, which are included within the scope of the present invention include ultrasound, other radio frequencies or mechanical intervention. Based on the disclosure herein, control of these types of interventional modalities will be known to those skilled in the art.

Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers, fibers or fiber bundles with lens tips as well as bundles of fibers with and without piercing tips and with or without firing tips, fiber ends having shaped or contoured end faces for selectively diverging the laser beam or other laser energy diverging means, rods, mirrors configurations and other laser delivery means with and without focusing lens and the like. It will also be understood that the apparatus and method of the present invention as described herein including the novel combination or use with of any conventional mechanism or method which are known to those skilled in the art, are included within the scope of this invention. Furthermore, with regard to non-laser TMR, a cannula or trocar assembly may be extended into the tissue of the left ventricle, with or without use of a mechanical piercing tool.

It will further be understood that while the present invention has been described for performing TMR on endocardial surfaces in the left ventricle, the apparatus and methods described herein are equally intended for use in any suitable procedure, including but not limited to procedures where any device need be extended through a guide catheter to a given surface on a given structure and extended into the structure a selected and controlled distance, for any medical procedures including laser treatment, tissue or organ visualzation, biopsy, etc. "Stimulation", for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A device for treatment of cardiovascular tissue comprising:

a catheter having at least one lumen and a distal end;

a treatment tool mounted within the at least one lumen and egressible from the distal end of the catheter;

an ultrasound transducer located at the distal end of the catheter, the transducer positioned to transmit ultrasound signals into tissue in a forward direction substantially axially aligned with an axis of the treatment tool, the transducer further receiving returning signals from the tissue;

a signal interface extending from the ultrasound transducer; and a signal processor connected to the signal interface, the signal processor performing real time determination of at least a first dynamic measurement of a distance between the transducer and at least one boundary surface of the tissue and a second dynamic measurement of an advancement distance of the treatment tool relative to the transducer.

2. The device of claim 1 further comprising a display device connected to the signal processor.

3. The device of claim 1 wherein the ultrasound transducer is an annular ring defining a generally central aperture therethrough.

4. The device of claim 1 wherein the treatment tool is a laser delivery device adapted for connection to a source of laser energy.

5. The device of claim 1 further comprising a source of laser energy connected to the treatment tool, the treatment tool comprising a laser delivery device.

6. The device of claim 4 wherein the laser delivery device is an optical fiber.

7. The device of claim 4 wherein the laser delivery device is a fiber optic bundle.

8. The device of claim 5 wherein the source of laser energy is a holmium laser.

9. The device of claim 5 wherein the source of laser energy is an excimer laser.

10. The device of claim 5 wherein the source of laser energy is a $CO_2$ laser.

11. The device of claim 1 wherein the treatment tool is a mechanical cutting device.

12. The device of claim 1 wherein the catheter is a pre-shaped tube having a lumen extending therethrough and the treatment tool is an optical fiber having a lens tip.

13. The device of claim 1 wherein the catheter has a proximal end attached to a handle and an inner tube within the lumen, the inner tube attached to the distal end of the catheter and slidable within the lumen, the handle having a deflection mechanism connected to deflection components extending between the deflection mechanism and the distal end.

14. The device of claim 1 wherein the ultrasound transducer comprises a piezoelectric crystal.

15. The device of claim 1 wherein the ultrasound transducer comprises a plurality of transducer elements.

16. The device of claim 1 wherein the signal interface is a coaxial cable.

17. The device of claim 1 wherein the signal processor performs real time determination of a third dynamic measurement of a distance between the advancing treatment tool and the at least one boundary surface.

18. The device of claim 1 wherein the signal processor performs real time determinations relative to two boundary surfaces of a tissue, the processor determining a substantially zero distance representing contact of the catheter with a first boundary surface, the processor further determining dynamic thickness between the first boundary surface and a second boundary surface, the processor further dynamically determining an advancement distance of the treatment tool from the first boundary surface and a remaining distance to the second boundary surface.

19. The device of claim 1 further comprising an alarm connected to the signal processor, the alarm activated when the signal processor detects a threshold distance between the treatment tool and the at least one boundary surface.

20. The device of claim 5 further comprising an interlock mechanism operatively attached to the source of laser energy and to the signal processor, the interlock mechanism deactivating delivery of laser energy to the laser delivery device upon determination of a threshold distance between the laser energy delivery device and the at least one tissue boundary.

21. The device of claim 1 further comprising an MIS tool having at least one lumen for guiding the catheter therethrough.

22. The device of claim 2 wherein the display generates an A-trace.

23. The device of claim 1 wherein the ultrasound transducer operates at a pulse repetition frequency of approximately 500 Hz to 10 kHz.

24. A method of monitoring tissue removal in tissue having a front boundary surface and a rear boundary surface, the method comprising the following steps:
(a) providing a device having a tissue removal tool with a treatment tip movably mounted within a catheter having a distal end, an ultrasound transducer mounted on the distal end, the device having a signal processing component operatively connected to the ultrasound transducer;
(b) positioning the catheter adjacent the front boundary surface of the tissue;
(c) moving the tissue removal tool within the catheter to position the treatment tip adjacent the tissue;
(d) transmitting ultrasound energy from the ultrasound transducer in a forward direction substantially aligned with an axis of the treatment tool into the tissue;
(e) receiving ultrasound signals reflected from at least the rear boundary surface of the tissue;
(f) determining the distance between the treatment tip of the tissue removal tool and the rear boundary surface of the tissue; and
(g) operating the tissue removal tool to remove tissue.

25. The method of claim 24 wherein step (g) further comprises controlling the removal of tissue based upon the distance determined in step (f).

26. The method of claim 24 in which the tissue removal tool is a laser delivery device adapted for connection to a source of laser energy, and step (b) positioning comprises introducing the catheter percutaneously into vasculature of a patient and advancing the catheter into a left ventricle of a beating heart until the catheter is positioned adjacent an endocardial surface.

27. The method of claim 24 in which the tissue removal tool is a laser delivery device adapted for connection to a source of laser energy, and step (b) positioning comprises introducing the catheter into the chest cavity and positioning the catheter adjacent an epicardial surface of a beating heart.

28. The method of claim 26 wherein step (f) further comprises determining the distance between the endocardial surface and the epicardial surface, the distance representing thickness of the myocardium.

29. The method of claim 28 wherein step (f) determines a dynamic thickness of the myocardium during contraction and expansion of the beating heart.

30. The method of claim 29 further comprising a display device connected to the signal processing component, the method further comprising the step of displaying the dynamic thickness determination to monitor a contraction phase and an expansion phase of the beating heart.

31. The method of claim 26 in which step (g) comprises mechanically piercing the tissue to a desired depth with the laser delivery device, the desired depth determined from the measurement in step (f); and, retracting the laser delivery device while simultaneously delivering laser energy to the tissue.

* * * * *